US011511260B2

(12) United States Patent
Wang et al.

(10) Patent No.: US 11,511,260 B2
(45) Date of Patent: Nov. 29, 2022

(54) OLEFIN EPOXIDATION CATALYST, PREPARATION METHOD THEREFOR, AND APPLICATION THEREOF

(71) Applicant: Wanhua Chemical Group Co., Ltd., Shandong (CN)

(72) Inventors: Tongji Wang, Shandong (CN); Fei Ye, Shandong (CN); Lei Wang, Shandong (CN); Naibo Chu, Shandong (CN); Lichao Yang, Shandong (CN); Kang Sun, Shandong (CN); Yuan Li, Shandong (CN); Weiqi Hua, Yantai (CN)

(73) Assignee: Wanhua Chemical Group Co., Ltd.

( * ) Notice: Subject to any disclaimer, the term of this patent is extended or adjusted under 35 U.S.C. 154(b) by 217 days.

(21) Appl. No.: 16/761,618

(22) PCT Filed: Jun. 29, 2018

(86) PCT No.: PCT/CN2018/093611
§ 371 (c)(1),
(2) Date: May 5, 2020

(87) PCT Pub. No.: WO2019/105031
PCT Pub. Date: Jun. 6, 2019

(65) Prior Publication Data
US 2021/0113990 A1    Apr. 22, 2021

(30) Foreign Application Priority Data
Nov. 29, 2017    (CN) .......................... 201711227008.1

(51) Int. Cl.
*B01J 21/06*    (2006.01)
*C07D 301/19*    (2006.01)
(Continued)

(52) U.S. Cl.
CPC ............. *B01J 21/08* (2013.01); *B01J 21/063* (2013.01); *B01J 35/1019* (2013.01);
(Continued)

(58) Field of Classification Search
CPC ...... B01J 21/08; B01J 21/063; B01J 35/1019; B01J 35/1061; B01J 37/0201; B01J 37/04;
(Continued)

(56) References Cited

U.S. PATENT DOCUMENTS 3,829,392 A    8/1974    Wulff
3,923,843 A    12/1975    Wulff
(Continued)

FOREIGN PATENT DOCUMENTS

CN    1248579 A    3/2000
CN    1250775 A    4/2000
(Continued)

OTHER PUBLICATIONS

International Search Report for Application No. PCT/CN2018/093611, dated Aug. 29, 2018, pp. 1-2.
(Continued)

*Primary Examiner* — Taylor V Oh
(74) *Attorney, Agent, or Firm* — Lerner, David, Littenberg, Krumholz & Mentlik, LLP (57) ABSTRACT

The present invention relates to a preparation method for an olefin epoxidation catalyst, comprising: (1) preparing a titanium-silicon gel; (2) performing pore-enlarging treatment to the titanium-silicon gel by using organic amine or liquid ammonia, and drying, calcinating to obtain a titanium-silicon composite oxide; (3) optionally performing alcohol solution of organic alkali metal salt treatment; and (4) optionally performing gas-phase silanization treatment. The catalyst prepared by the method of the present invention has
(Continued)

adjustable variability for pore size, so that the activity thereof for epoxidation reactions of the olefin molecules with different dynamic diameters is higher; the surface acidity of the catalyst can be reduced effectively through two-step modification to the catalyst, so that the catalyst has higher selectivity for epoxidation product.

18 Claims, 1 Drawing Sheet

(51) Int. Cl.
  *B01J 21/08*   (2006.01)
  *B01J 35/10*   (2006.01)
  *B01J 37/02*   (2006.01)
  *B01J 37/04*   (2006.01)
  *B01J 37/08*   (2006.01)

(52) U.S. Cl.
  CPC ....... *B01J 35/1061* (2013.01); *B01J 37/0201* (2013.01); *B01J 37/04* (2013.01); *B01J 37/088* (2013.01); *C07D 301/19* (2013.01)

(58) Field of Classification Search
  CPC .. B01J 37/088; B01J 2229/32; B01J 37/0018; B01J 37/033; B01J 23/04; C07D 301/19; C07D 303/04
  USPC .......................................... 549/529; 502/242
  See application file for complete search history.

(56) References Cited

U.S. PATENT DOCUMENTS

| | | | |
|---|---|---|---|
| 4,021,454 A | 5/1977 | Wulff et al. | |
| 5,783,167 A | 7/1998 | Corma Canos et al. | |
| 6,096,910 A | 8/2000 | Yamamoto et al. | |
| 6,211,388 B1 | 4/2001 | Tsuji et al. | |
| 6,323,147 B1 | 11/2001 | Yamamoto et al. | |
| 6,465,382 B1 | 10/2002 | Strebelle et al. | |

FOREIGN PATENT DOCUMENTS

| | | |
|---|---|---|
| CN | 1328878 A | 1/2002 |
| CN | 101348472 A | 1/2009 |
| CN | 101429176 A | 5/2009 |
| CN | 101602013 A | 12/2009 |
| CN | 101747296 A | 6/2010 |
| CN | 102745711 A | 10/2012 |
| CN | 104437636 A | 3/2015 |
| CN | 106582809 A | 4/2017 |
| CN | 107930610 A | 4/2018 |
| EP | 3702027 A1 | 9/2020 |
| JP | 2001522716 A | 11/2001 |

OTHER PUBLICATIONS

Muller C A et al: "Amine-modified titania-silica hybrid gels as epoxidation catalysts". Applied Catalysis A: General. Elsevier. Amsterdam. NL. vol. 201. No. 2. Jul. 10, 2000 (Jul. 10, 2000); pp. 253-261. XP004272408. ISSN: 0926-860X. DOI: 10.1016/S0926-860X(00)00446-4.

Extended European Search Report including Written Opinion for EP18884023.5 dated Jun. 28, 2021; 7 pages.

Sayari A, Yang Y, Kruk M, Jaroniec M. Expanding the pore size of MCM-41 silicas: use of amines as expanders in direct synthesis and postsynthesis procedures. The Journal of Physical Chemistry B. May 6, 1999;103(18):3651-8.

Hearing Notice for Indian Application No. 202047018750 dated Jun. 5, 2021; 2 pages.

Notification of Reasons for Refusal for Japanese Application No. 2020529290 dated Jul. 6, 2021; 2 pages.

OLEFIN EPOXIDATION CATALYST, PREPARATION METHOD THEREFOR, AND APPLICATION THEREOF

CROSS REFERENCE TO RELATED APPLICATIONS

The present application is a national phase entry under 35 U.S.C. § 371 of International Application No. PCT/CN2018/093611, filed Jun. 29, 2018, which claims priority from Chinese Patent Application No. 201711227008.1 filed Nov. 29, 2017, all of which are hereby incorporated herein by reference.

TECHNICAL FIELD

The present invention relates to a preparation method for an olefin epoxidation catalyst, and specifically relates to a preparation method for a titanium-silicon composite oxide catalyst. The present invention also relates to an olefin epoxidation catalyst prepared by the said preparation method and use thereof for olefin epoxidation reaction.

BACKGROUND ART

For the epoxy resins, surfactants, coatings, binders, surface coating reagents and other chemicals widely used in life and industry, there is a great demand for epoxides which belong to one type of commonly used intermediate materials for the synthesis of these chemicals. The traditional production processes for synthesizing epoxides are usually chlorohydrination methods or co-oxidation methods, but these methods are with the disadvantages of heavy pollution, largely corrosion to equipments, more by-products, high cost and so on.

Therefore, a lot of companies both at home and abroad are committed to develop green production technologies of olefin epoxidation with simple, clean and economical processes. The production technology that $H_2O_2$, tert-butyl hydrogen peroxide (TBHP), ethylbenzene hydrogen peroxide (EBHP) or cumyl hydroperoxide (CHP) is used as oxidant to react with olefins to produce epoxides is one of the development directions. The core of this technology is olefin epoxidation catalysts, the structure parameters and the compositions of the catalysts are able to directly affect the conversion rates of raw materials and the selectivity of products.

For the development of green production processes of olefin epoxidation, the core thereof lies in the development of a catalyst with high activity and selectivity for epoxidation, good stability, applicability for various olefin reactants systems, and a preparation method which can be achieved easily. Since the 1980s, researches on heterogeneous olefin epoxidation catalysts have been started at home and abroad, among which, titanium silicalite molecular sieve is a type of representative catalyst due to good catalytic activity for selective oxidation of olefins. Among the titanium heteroatom containing molecular sieves developed in the early 1980s, TS-1, TS-2 etc. are the representative ones, such catalysts are generally microporous (for example, the pore size is about 0.55 nm) and the pore canals thereof are small. As oxidants and olefins are able to conduct catalytic reactions at Ti active center to produce epoxides only after their diffusions in the pore canals of the titanium silicalite molecular sieves, therefore, this type of molecular sieves such as TS-1 and TS-2 are only suitable for the reactions of micromolecule olefins with $H_2O_2$ as oxidant. However, for the reactions of macromolecule olefins with higher carbon numbers with ethylbenzene hydrogen peroxide or cumyl hydroperoxide as oxidant, it is difficult for the reactants to conduct catalytic reactions by diffusing in the micropores of the titanium silicalite molecular sieves due to their large molecular dynamic diameters.

Therefore, the development of titanium silicalite catalysts with large pore sizes has become one of the hot topics in the industry. For example, patent applications CN 1250775A and CN 1248579A disclose a process of propylene epoxidation for producing epoxypropane by using ethylbenzene hydrogen peroxide as oxidant and Ti-MCM-41 molecular sieve as catalyst. US patent application U.S. Pat. No. 5,783,167 discloses a method for synthesizing titanium containing mesoporous material Ti-MCM-41 through hydrothermal method, and patent application U.S. Pat. No. 6,323,147 discloses a process for preparing epoxypropane by using cumyl hydroperoxide as oxidant and Ti-MCM-41 molecular sieve as catalyst. Sumitomo corporation of Japan also discloses a synthesis method for titanium containing catalyst Ti-MCM-41 with a mesoporous structure. Patent application CN 106582809A discloses a synthesis method for a modified titanium silicalite molecular sieve with a pore diameter of above 10 nm. Hydrothermal method is employed in all the above methods to synthesize the catalysts, titanium silicalite catalysts with large pore sizes (>2.0 nm) are prepared under the conditions of high temperature and hydrothermal by using the template agents with specific molecular weights and structures. The synthesis processes for this type of mesoporous molecular sieves are complex, plenty of template agents are needed during the synthesis process, as a result the preparation cost of these catalysts is high, the applications in industry thereof are limited.

In addition, patent applications U.S. Pat. Nos. 3,829,392, 3,923,843 and 4,021,454 disclose a titanium silicalite catalyst which is obtained by using macroporous $SiO_2$ as carrier, loading titanium source onto the surface of the carrier through vapour deposition method or liquid-phase impregnation method, and then subjecting to drying, calcinating, silanization treatment and other steps. As the titanium source used is easy to be hydrolyzed during the loading process, acidic free-state $TiO_2$ is formed. Moreover, it is difficult to increase the loading amount of titanium when the catalyst is prepared by impregnation method, which leads to low catalytic activity and low conversion rate of olefin in the process of olefin epoxidation.

At present, the preparation methods for titanium-silicon composite oxide catalysts mainly comprise vapor deposition method and sol-gel method. The following disadvantages are existed in both vapor deposition method and sol-gel method: the preparation processes are complex, the operations are complicated, the conditions are harsh and difficult to be controlled, and the reaction time is long. In addition, once the conditions are under improper control, the obtained catalysts tend to form more titanium compounds (mainly is free-state titanium dioxide) out of framework, the surface acidity of the catalysts is strong, when they are used in propylene epoxidation reactions, the effective utilization rates of organic peroxides will become lower.

To sum up, at present the conventional microporous titanium silicalite molecular sieves have very low activity for the epoxidation reactions of macromolecule olefins with C6 or above due to the small pore sizes, their applications in olefin epoxidation reactions are limited. Mesoporous molecular sieve materials such as Ti-MCM-41 and Ti-SBA-15 are available for the epoxidation reactions of macromolecule olefins with EBHP or CHP as oxidant. However, such catalysts are difficult to be synthesized and the template agents used are difficult to be prepared and expensive, the resulted cost is very high, and the applications in industry thereof are limited. The titanium silicalite catalysts prepared with $SiO_2$ as carrier through vapor deposition method or liquid-phase impregnation method have low catalytic selectivity and reaction activity due to the acidic free-state $TiO_2$ existing on the surface thereof and the low loading amount of Ti active center.

SUMMARY OF THE INVENTION

Therefore, in this art it is necessary to provide an epoxidation catalyst with high activity and selectivity for the epoxidation reactions of olefin molecules, especially those with large dynamic diameters.

On the other hand, in this art it is also necessary to provide a preparation method for the olefin epoxidation catalyst, the preparation method requires low cost, the preparation process thereof is relatively simple, in addition, the preparation method can be adjusted and applied flexibly, through adjusting reaction conditions, the relevant olefin epoxidation catalysts which have high activity and selectivity for the epoxidation reactions of the olefin molecules with different dynamic diameters can be obtained.

In order to solve the above-mentioned technical problems, the present invention provides a preparation method for an olefin epoxidation catalyst, comprising the following steps:

(1) mixing a silicon ester solution, a titanium ester solution and a surfactant, adjusting pH to 6~7 by using diluted acid in order to achieve a complete hydrolysis of the silicon ester, and aging to obtain a titanium-silicon composite gel; in some preferred embodiments, the diluted acid may be $HNO_3$, formic acid, acetic acid etc. with a concentration of 2~10 wt %;

(2) adding organic amine or liquid ammonia to the gel, performing pore-enlarging treatment under constant temperature condition with a treatment temperature of 60~150° C., and drying, calcinating in air atmosphere to obtain an amorphous titanium-silicon composite oxide;

(3) optionally, subjecting the titanium-silicon composite oxide to impregnation by using an alcohol solution of organic alkali metal salt, and drying, calcinating in air atmosphere to obtain a titanium-silicon composite oxide modified by alkali metal;

(4) optionally, subjecting the titanium-silicon composite oxide obtained in step (2) or the titanium-silicon composite oxide modified by alkali metal obtained in step (3) to a gas-phase silanization treatment by using an organic silanization reagent with $N_2$ as carrier gas;

to give the olefin epoxidation catalyst of the present invention.

For the preparation method of the present invention, wherein:

in step (1), the surfactant is added to serve as a dispersing agent and a pore-forming agent in the synthesis process, so that a better mixture of the titanium ester solution and the silicon ester solution may be achieved, and a certain number of disordered pore canals in the titanium-silicon composite oxide may be formed at the same time;

in step (2), the pore size of the gel may be enlarged through the pore-enlarging treatment, which may be adjusted by controlling treatment temperature and treatment time, the higher the treatment temperature is and the longer the treatment time is, the larger the obtained pore size is; in addition, the constant temperature may be achieved by using, for example, a constant temperature hydrothermal kettle;

in step (3), during the impregnation process, the alkali metal ions interact with the carrier surface and the hydroxyl groups dissociated from free-state $TiO_2$, so that the alkali metal ions may exchange with $H^+$ dissociated from the carrier surface to achieve the effect of reducing the acidity of the carrier surface;

in step (4), the gas-phase silanization treatment may be performed in any reactor known in this art, preferably in a tubular furnace.

As a preferred embodiment of the preparation method for an olefin epoxidation catalyst according to the present invention: in step (1), the molar ratio of the silicon ester to the titanium ester is 10~60:1, and the addition amount of the surfactant is 0.5~5.0 wt % based on the total weight of the silicon ester and the titanium ester;

in step (2), the mass ratio of the organic amine or liquid ammonia to the gel is 1:5~1:10, and the treatment time of the pore-enlarging treatment is 3~12 h, the amorphous titanium-silicon composite oxide with an average pore size of 5~20 nm is obtained accordingly;

further preferably, in step (3), the concentration of the alcohol solution of organic alkali metal salt is 2~5 wt %; the mass ratio of the alcohol solution of organic alkali metal salt to the titanium-silicon composite oxide is 5:1~0:1; the impregnation temperature is 40~80° C., preferably 50~70° C., and the impregnation time is 1~5 h, preferably 2~4 h;

preferably, in step (4), the weight ratio of the organic silanization reagent to the titanium-silicon composite oxide or the titanium-silicon composite oxide modified by alkali metal in step (3) is 0.01~0.2; the temperature for the gas-phase silanization treatment is 200~400° C. and the treatment time is 2~6 h.

In a preferred embodiment of the preparation method for an olefin epoxidation catalyst according to the present invention, in step (1), i) the silicon ester is one or more selected from the group consisting of tetraethyl silicate, ethyl orthosilicate and butyl silicate; the mass concentration of the silicon ester solution is 30~60 wt % wherein the solvent may be a suitable solvent known in this art, preferably ethanol or isopropanol, both of which may inhibit the hydrolysis of the silicon ester and make the added surfactant better dispersed in the system;

ii) the titanium ester is one or more selected from the group consisting of tetraethyl titanate, tetrapropyl titanate, tetrabutyl titanate, tetraisopropyl titanate etc.; the concentration of the titanium ester solution is 10~30 wt % wherein the solvent is n-butanol or isopropanol;

iii) the surfactant is one or more selected from the group consisting of CTAB (hexadecyl trimethyl ammonium bromide), P-123 (triblock copolymer), sodium dodecyl sulfonate, polyacrylamide, polyethylene glycol and polypropylene glycol;

iv) the diluted acid is one selected from the group consisting of nitric acid, hydrochloric acid and acetic acid.

In a preferred embodiment of the preparation method for an olefin epoxidation catalyst according to the present invention, in step (1), the surfactant is firstly added to the silicon ester solution and mixed evenly, then the titanium ester solution is slowly added to the silicon ester solution under the condition that the stirring speed of a stirring reactor is 3000~5000 r/min, so that the titanium ester solution may quickly achieve an uniform dispersion in the system to ensure the uniformity of the gel.

In a preferred embodiment of the preparation method for an olefin epoxidation catalyst according to the present invention, in step (1), the aging temperature is 40~120° C. and the aging time is 2~8 h.

In a preferred embodiment of the preparation method for an olefin epoxidation catalyst according to the present invention, in step (2), the organic amine is one or more selected from the group consisting of ethylamine, ethylenediamine, propylamine, and n-butylamine.

In a preferred embodiment of the preparation method for an olefin epoxidation catalyst according to the present invention, in step (2), the drying temperature is 80~160° C. and the drying time is 3~6 h; the calcinating temperature is 400~600° C., preferably 450~550° C., and the calcinating time is 3~6 h.

In a preferred embodiment of the preparation method for an olefin epoxidation catalyst according to the present invention, in step (3), the organic alkali metal salt is one or more selected from the group consisting of sodium methoxide, sodium ethoxide, potassium ethoxide, sodium tert-butoxide and potassium tert-butoxide; the alcohol used as solvent in the alcohol solution of the organic alkali metal salt is one or more selected from the group consisting of methanol, ethanol and tert-butanol.

In a preferred embodiment of the preparation method for an olefin epoxidation catalyst according to the present invention, in step (3), the drying temperature is 80~160° C. and the drying time is 3~6 h; the calcinating temperature is 300~500° C. and the calcinating time is 3~6 h.

In a preferred embodiment of the preparation method for an olefin epoxidation catalyst according to the present invention, in step (4), the organic silanization reagent is one or more selected from the group consisting of hexamethyldisilazane, hexamethylchlorosilazane, heptamethylchlorosilazane, trimethylchlorosilane, dimethylchlorosilane, tetramethyldisilazane, dimethyldiethoxysilane, trimethylmethoxysilane, dimethyldimethoxysilane and trimethylethoxysilane, preferably hexamethyldisilazane.

Another aspect of the present invention is to provide an olefin epoxidation catalyst which is an amorphous titanium-silicon composite oxide, wherein, the molar ratio of $SiO_2$ to $TiO_2$ contained is 10~60:1 by stoichiometry, optionally, alkali metal element and/or silane group are additionally comprised in the catalyst with a mass percentage of 1~10% respectively; the titanium-silicon composite oxide has an average pore size of 5~20 nm, and a specific surface area of 200~600 $m^2/g$, preferably 300~450 $m^2/g$.

Preferably, the olefin epoxidation catalyst of the present invention is prepared by the above-mentioned preparation method for an olefin epoxidation catalyst.

The performance evaluation of the catalyst of the present invention may be conducted in a reaction kettle or a fixed-bed reactor, the process conditions of the evaluation in a fixed-bed reactor are as follows: the mass space velocity of olefin feed is 2~8 $h^{-1}$, the molar ratio of olefin to peroxide is 2~20, preferably 4~8, the concentration of peroxide solution is 20~40 wt %, the reaction pressure is 0~4 MPa, and the reaction temperature is 60~120° C.; the process conditions of the evaluation in a reaction kettle are as follows: the molar ratio of olefin to peroxide is 2~20, preferably 4~8, the concentration of the catalyst in reaction solution is 0.5 wt %~5 wt %, the reaction time is 1~4 h, the reaction pressure is 0~4 MPa, and the reaction temperature is 60~120° C.

Another aspect of the present invention is to provide use of the above-mentioned catalyst for olefin epoxidation reaction, the olefin is preferably C3~C16 linear or isomerized olefin, C6~C16 cycloolefin or aromatic olefin, the oxidant is preferably TBHP (tert-butyl hydrogen peroxide), EBHP (ethylbenzene hydrogen peroxide) or CHP (cumyl hydroperoxide), or other organic peroxides, and the epoxidation reaction is preferably a liquid-phase epoxidation reaction of the olefin and the organic peroxide.

The term "optionally" used in the present invention means a step that may or may not be performed, or means an ingredient that may or may not be comprised.

The positive effects of the present invention lie in that:

1. a preparation method for the olefin epoxidation catalyst is provided by the present invention through organic amine or liquid ammonia treatment to adjust the pore size so as to make the pore size possessing adjustable variability, the obtained catalyst is an amorphous titanium-silicon composite oxide, the average pore size range thereof is 5~20 nm, which is greater than those of conventional microporous and mesoporous titanium silicalite molecular sieves (the pore sizes of microporous and mesoporous molecular sieves commonly are 0.5~0.8 nm and 1~2 nm respectively), so that the olefin molecules with different dynamic diameters and TBHP, EBHP, CHP or other organic peroxides can contact with Ti active center sufficiently in the pore canals, thereby the catalyst has higher reactivity.

2. in the catalyst preparation method of the present invention, it is preferred to use the alcohol solution of organic alkali metal salt to modify the titanium-silicon composite oxide prepared as described above, without using water as solvent in the treatment process, free-state $TiO_2$ formed from the hydrolysis of framework titanium can be avoided; it is further preferred to use the organic silanization reagent for gas-phase silanization treatment. The above mentioned two treatment means can effectively reduce the surface acidity of the catalyst and consequently reduce the ability of the catalyst to promote the decomposition of the peroxide and the polymerization of the olefin, the effects of the catalyst on improving epoxidation selectivity and anti-coking ability are therefore achieved.

3. the catalyst of the present invention can catalyze the epoxidation reactions of organic peroxides, such as TBHP, EBHP or CHP, with olefins, such as C3~C16 linear or isomerized α-olefins, C6~C16 cycloolefins or aromatic olefins, especially propylene, isobutylene, 1-decylene, cyclododecatriene, styrene, under mild reaction conditions, so that both the conversion rates of the peroxides reacted and the selectivity for epoxidation products are high, in some preferred embodiments, the conversion rates of the peroxides can be up to ≥99.0%, and the selectivity for epoxidation products can be up to ≥93%.

4. for the catalyst of the present invention, the cost of raw materials is low, the preparation process is simple, and it is easy to achieve an expanded production.

DETAILED DESCRIPTION

In order to understand the present invention better, the present invention will be further illustrated below with reference to the Examples, but the content of the present invention is not limited thereto.

In the Examples, the hydrothermal reaction kettle used in the catalyst preparation process is produced by Yantai Keli Chemical Equipment Co., Ltd. All reagents are commercially available.

The structures and properties of the prepared catalysts were determined by using the following analysis and test methods: 1. Determination of the average pore size and the specific surface area of each catalyst The average pore size and the specific surface area of each catalyst prepared in Examples and Comparative Examples were determined by a physical adsorption instrument which is produced by Micromeritics Corporation with a type of ASAP2020.

2. Confirmation of the amorphous structure of the catalyst

The structure of the catalyst prepared in Example 1 was determined by an X-ray diffractometer which is produced by PANalytical Corporation with a type of X'pert³powder.

3. Confirmation of the modification and the content of alkali metal

Each catalyst prepared in Examples and Comparative Examples was analyzed by XRF to confirm whether the alkali metal element modification process described in step (3) was realized and the content of the alkali metal element. The instrument is produced by Shimadzu Corporation of Japan with a type of EDX-LE.

4. Confirmation of the silanization modification and the silane group content

The catalysts prepared in Example 1 and Comparative Example 3 were thermal analyzed by using a scanning calorimeter to obtain the DSC curves in order to confirm whether the silanization modification process described in step (4) was realized. The scanning calorimeter is produced by Mettler-Toledo Corporation with a type of DSC1 Pro.

The silane group content of each catalyst prepared in Examples and Comparative Examples was determined by using a thermogravimetric analyzer (TGA), the mass loss of the catalyst at >400° C. was considered as the silane group content. The instrument is produced by Shimadzu Corporation of Japan with a type of DTG-60.

5. Determination of the conversion rate of peroxide in epoxidation reaction

The conversion rate of peroxide in epoxidation reaction performed by using each catalyst prepared in Examples and Comparative Examples was obtained through iodimetry analysis, where the potentiometric titrator used in the titration step is manufactured by Metrohm Corporation of Switzerland with a type of 916 Ti-Touch.

Specific steps of the iodimetry:

(1) 20 mL of glacial acetic acid was added to a conical flask, and about 5 g of KI was added too after the evacuating of $N_2$;

(2) about 1 g of sample for analysis was taken and added into the above mixture, and blank sample was prepared as a contrast;

(3) after water sealing, magnetic stirring was performed in dark to react for 30 min;

(4) 50 mL of pure water was added, $Na_2S_2O_3$ solution with a confected concentration was employed for titration;

(5) the total mole number of an organic peroxide was calculated according to the usage amount of the $Na_2S_2O_3$ solution, and the conversion rate thereof was calculated consequently.

Total mole number of organic peroxide =

$$\frac{1}{2} V_{Na_2S_2O_3} + C_{Na_2S_2O_3} \times \frac{\text{total quality of mixture in reaction system}}{\text{sample quality}}$$

Wherein, $V_{Na2S2O3}$ represents the volume of the consumed $Na_2S_2O_3$ solution, $C_{Na2S2O3}$ represents the molar concentration of the used $Na_2S_2O_3$ solution.

Conversion rate (%) =

$$\frac{\text{total mole number of organic peroxide before reaction} - \text{total mole number of organic peroxide after reaction}}{\text{total mole number of organic peroxide before reaction}} \times 100\%$$

6. Determination of the selectivity for epoxidation product in epoxidation reaction The selectivity for epoxidation product in epoxidation reaction performed by using each catalyst prepared in Examples and Comparative Examples was analyzed and determined through gas chromatography.

The conditions of chromatography analysis are shown in the Table below:

TABLE 1

| Operating conditions of chromatography | |
|---|---|
| Item | Parameter |
| Chromatographic column | Agilent 19091N-133 (30 m* 2501 μm* 0.25 μm) |
| Flow rate of $H_2$ | 35 mL/min |
| Flow rate of air | 350 mL/min |
| Flow rate of make-up gas ($N_2$) | 25 mL/min |
| Heater | 270° C. |
| Column oven | 250° C. |
| Temperature-rise procedure | Initial temperature: 50° C. Temperature programming: 50-100° C., 15° C./min, maintained for 0 min; 100-250° C., 20° C./min, maintained for 2 min. |
| Split ratio of injection port | 30:1 |
| Temperature of FID detector | 270° C. |

The content of epoxidation product was determined by internal standard method, the concentration of epoxidation product was determined by using DMF (dimethylformamide) as solvent and DT (dioxane) as internal standard substance. Pure epoxidation product as an object to be tested was prepared to form standard solutions with different mass concentrations by using DMF as solvent, each standard solution with a fixed mass was taken to mix with the internal standard substance respectively, followed by injection for analysis. For each standard solution, the peak area ratio of epoxidation product to DT in the chromatogram was x, and the mass concentration (%) of epoxidation product in each standard solution was y, and an internal standard curve y=(ax−b)×100% was obtained, ensuring that $R^2$ coefficient was ≤0.999. Then, the mixture in the system after reaction was sampled, the sample was diluted with an internal standard substance solution and analyzed by gas chromatography, therein, the quality of the internal standard substance in the diluted solution to be tested was equal to that used for drawing standard curve, and the total quality of the diluted solution to be tested was equal to that of the injection for drawing standard curve.

Mass concentration of epoxidation product=
($a \times (A_{epoxidation\ product}/A_{DT})-b) \times$ dilution ratio$\times 100\%$ Wherein, A represents the corresponding peak area of the subscript substance thereof in the chromatogram; dilution ratio represents the multiple of the volume of the diluted solution to be tested relative to the volume of the sample before dilution.

Content of epoxidation product in sample=mass concentration of epoxidation product$\times$sample quality Selectivity for epoxidation product=total quality of epoxidation product/quality of epoxide capably obtained from oxidation of olefin by actual converted peroxide (EBHP, CHP etc.) in theory$\times$100%

EXAMPLE 1

(1) Preparation of Titanium-Silicon Gel 300 g of ethyl orthosilicate and 200 g of ethanol were added into a 1 L reaction kettle, the stirring speed was adjusted to 300 r/min at room temperature, 6.5 g of CTAB (hexadecyl trimethyl ammonium bromide) was added and followed by stirring for 1 h; 32.85 g of tetraethyl titanate was dissolved in 131.41 g of isopropanol, the stirring speed of the reaction kettle was increased to 3000 r/min, the obtained titanium ester solution was slowly added to a hydrothermal kettle and stirred vigorously for 1.5 h. The stirring speed was reduced to 100 r/min, pH was adjusted to 6~6.5 by dropping $HNO_3$, the aging was lasted for 8 h at 60° C., and a titanium-silicon composite gel was prepared with a stoichiometric composition of $TiO_2.10SiO_2.(H_2O)_x$.

(2) Pore-Enlarging Treatment 100 g of the gel prepared in step (1) was transferred into a high-pressure stainless-steel hydrothermal kettle, 20 g of ethylamine liquid was added, the treatment was performed at a constant temperature of 60° C. for 6 h. The gel treated by ethylamine was dried in air atmosphere at 120° C. for 3 h, and then calcinated in air at 550° C. for 3 h to give a titanium-silicon composite oxide, the specific surface area thereof determined by BET was 422 $m^2/g$ and the average pore size thereof was 6.5 nm.

(3) Alkali Metal Modification 2 g of potassium ethoxide was dissolved in 98 g of anhydrous ethanol to form an impregnating solution, which was added to the flask of a rotary evaporator, 20 g of the titanium-silicon composite oxide was added too, and rotated and impregnated for 3 h at 60° C. to perform an ion exchange reaction by alkali metal treatment; when the reaction was completed, a titanium-silicon composite oxide modified by alkali metal was obtained after drying for 5 h at 100° C. in air and calcinating for 3 h at 500° C. in air.

(4) Gas-Phase Silanization Treatment 20 g of the titanium-silicon composite oxide modified by alkali metal was transferred into a tube furnace, and high purity $N_2$ (purity is above 99.995%) was used as carrier gas, 3 g of hexamethyldisilazane was inlet and then reacted for 3 h at 250° C., Catalyst A was prepared.

EXAMPLE 2

A titanium-silicon composite gel was prepared according to Example 1, the difference therebetween lay in that in the pore-enlarging treatment process, 20 g of ethylenediamine liquid was added and the treatment was performed at a constant temperature of 90° C. for 10 h, the processed gel was then dried at 120° C. for 3 h and calcinated at 550° C. for 3 h to give a titanium-silicon composite oxide, the specific surface area thereof determined by BET was 368 $m^2/g$ and the average pore size thereof was 10.7 nm. The titanium-silicon composite oxide was then subjected to the alkali metal modification and the gas-phase silanization treatment under the same conditions as Example 1 to give Catalyst B.

EXAMPLE 3

A titanium-silicon composite gel was prepared according to Example 1, the difference therebetween lay in that in the pore-enlarging treatment process, 20 g of high purity liquid ammonia (purity is above 99.99%) was added and the treatment was performed at a constant temperature of 150° C. for 12 h, the processed gel was then dried at 160° C. for 3 h and calcinated at 550° C. for 3 h to give a titanium-silicon composite oxide, the specific surface area thereof determined by BET was 322 $m^2/g$ and the average pore size thereof was 18.3 nm. The titanium-silicon composite oxide was then subjected to the alkali metal modification and the gas-phase silanization treatment under the same conditions as Example 1 to give Catalyst C.

EXAMPLE 4

300 g of ethyl orthosilicate and 200 g of ethanol were added into a 1 L reaction kettle, the stirring speed was adjusted to 300 r/min at room temperature, 6.5 g of CTAB (hexadecyl trimethyl ammonium bromide) was added and followed by stirring for 1 h; 8.17 g of tetrabutyl titanate was dissolved in 32.67 g of isopropanol, the stirring speed of the reaction kettle was increased to 3000 r/min, the obtained titanium ester solution was slowly added to a hydrothermal kettle and stirred vigorously for 1.5 h. The stirring speed was reduced to 100 r/min, pH was adjusted to 6~6.5 by dropping $HNO_3$, the reactants were aged for 8 h at 60° C., and a titanium-silicon composite gel was prepared with a stoichiometric composition of $TiO_2.60SiO_2.(H_2O)_x$.

The obtained titanium-silicon composite gel was then subjected to the pore-enlarging treatment, the alkali metal modification and the gas-phase silanization treatment according to the method of Example 1 to give Catalyst D, the specific surface area thereof determined by BET was 406 $m^2/g$ and the average pore size thereof was 6.2 nm.

EXAMPLE 5

A titanium-silicon composite gel was prepared and then subjected to the pore-enlarging treatment according to the method described in Example 3, after drying and calcinating, a titanium-silicon composite oxide was obtained. The difference therebetween lay in that in the process of alkali metal modification, 5 g of potassium tert-butoxide was dissolved in 95 g of anhydrous tert-butanol, and 20 g of the titanium-silicon composite oxide was added too, then rotated and impregnated for 3 h at 80° C. to perform an ion exchange reaction by alkali metal treatment; when the reaction was accomplished, a titanium-silicon composite oxide modified by alkali metal was obtained after drying for 5 h at 100° C. in air and calcinating for 3 h at 500° C. in air, which was then subjected to the same gas-phase silanization treatment as Example 1 to give Catalyst E, the specific surface area thereof determined by BET was 305 m²/g and the average pore size thereof was 18.5 nm.

EXAMPLE 6

A titanium-silicon composite gel was prepared according to the method described in Example 1, and then subjected to the pore-enlarging treatment according to the method described in step (2) of Example 1, after drying and calcinating, a titanium-silicon composite oxide was obtained. Then the modification was performed by using an alcohol solution of organic alkali metal salt, the modification process comprised that: 2 g of potassium ethoxide was dissolved in 98 g of anhydrous ethanol to form an impregnating solution, which was added to the flask of a rotary evaporator, 20 g of the titanium-silicon composite oxide was added too, and then rotated and impregnated for 3 h at 60° C. to perform an ion exchange reaction by alkali metal treatment; when the reaction was accomplished, a catalyst which was not subjected to silanization treatment was obtained and recorded as F after drying for 5 h at 100° C. in air and calcinating for 3 h at 500° C. in air, the specific surface area thereof determined by BET was 407 m²/g and the average pore size thereof was 6.7 nm.

EXAMPLE 7

A titanium-silicon composite gel was prepared according to the method described in Example 1, and then subjected to the pore-enlarging treatment according to the method described in step (2) of Example 1, after drying and calcinating, a titanium-silicon composite oxide was obtained. Then 20 g of the titanium-silicon composite oxide without alkali metal modification was directly transferred into a tube furnace, high purity $N_2$ was used as carrier gas, 3 g of hexamethyldisilazane was inlet and then reacted for 3 h at 250° C., a catalyst which was not subjected to alkali metal modification was obtained and recorded as G, the specific surface area thereof determined by BET was 411 m²/g and the average pore size thereof was 6.6 nm.

EXAMPLE 8

A titanium-silicon composite gel was prepared and then subjected to the pore-enlarging treatment according to the method described in Example 1, after drying and calcinating, a titanium-silicon composite oxide was obtained. The difference therebetween lay in that in the process of alkali metal modification, 2.4 g of potassium nitrate was dissolved in 95 g of deionized water, and 20 g of the titanium-silicon composite oxide was added too, then rotated and impregnated for 3 h at 80° C. to perform an ion exchange reaction by alkali metal treatment; when the reaction was accomplished, a titanium-silicon composite oxide modified by alkali metal was obtained after drying for 5 h at 100° C. and calcinating for 3 h at 500° C. 20 g of the titanium-silicon composite oxide modified by alkali metal was transferred into a tube furnace, high purity $N_2$ was used as carrier gas, 3 g of hexamethyldisilazane was inlet and then reacted for 3 h at 250° C., a catalyst was obtained and recorded as H, the specific surface area thereof determined by BET was 387 m²/g and the average pore size thereof was 6.7 nm.

COMPARATIVE EXAMPLE 1

300 g of ethyl orthosilicate and 200 g of ethanol were added into a 1 L reaction kettle, the stirring speed was adjusted to 300 r/min at room temperature, 6.5 g of CTAB (hexadecyl trimethyl ammonium bromide) was added and stirred for 1 h; 32.85 g of tetraethyl titanate was dissolved in 131.41 g of isopropanol, the stirring speed of the reaction kettle was increased to 3000 r/min, the obtained titanium ester solution was slowly added to a hydrothermal kettle and stirred vigorously for 1.5 h. The stirring speed was reduced to 100 r/min, pH was adjusted to 6~6.5 by dropping $HNO_3$, the reactants were aged for 8 h at 60° C., and a titanium-silicon gel was prepared with a composition of $TiO_2.10SiO_2.(H_2O)_x$. The obtained gel without subjecting to pore-enlarging treatment and alkali metal modification treatment was directly dried at 100° C. for 5 h and calcinated at 500° C. for 3 h to give a titanium-silicon composite oxide. 20 g of the titanium-silicon composite oxide was transferred into a tube furnace, high purity $N_2$ was used as carrier gas, 3 g of hexamethyldisilazane was inlet and then reacted for 3 h at 250° C., a catalyst was obtained and recorded as DB-1, the specific surface area thereof determined by BET was 413 m²/g and the average pore size thereof was 2.7 nm.

COMPARATIVE EXAMPLE 2

A titanium-silicon gel was prepared according to the method described in Example 1 and a titanium-silicon composite oxide was directly obtained without subjecting to pore-enlarging treatment, which was then modified by using an alcohol solution of organic alkali metal salt, the modification process comprised that: 2 g of potassium ethoxide was dissolved in 98 g of anhydrous ethanol to form an impregnating solution, which was added to the flask of a rotary evaporator, 20 g of the titanium-silicon composite oxide was added too, and rotated and impregnated for 3 h at 60° C. to perform an ion exchange reaction by alkali metal treatment; when the reaction was accomplished, a titanium-silicon composite oxide modified by alkali metal was obtained after drying for 5 h at 100° C. in air atmosphere and calcinating for 3 h at 500° C. in air. 20 g of the titanium-silicon composite oxide modified by alkali metal was transferred into a tube furnace, high purity $N_2$ was used as carrier gas, 3 g of hexamethyldisilazane was inlet and then reacted for 3 h at 250° C., a catalyst was obtained and recorded as DB-2, the specific surface area thereof determined by BET was 405 m²/g and the average pore size thereof was 2.6 nm.

COMPARATIVE EXAMPLE 3

A titanium-silicon composite gel was prepared according to the method described in Example 1 and a titanium-silicon composite oxide was directly obtained without subjecting to pore-enlarging treatment. Then the modification was performed by using an alcohol solution of organic alkali metal salt, the modification process comprised that: 2 g of potassium ethoxide was dissolved in 98 g of anhydrous ethanol to form an impregnating solution, which was added to the flask of a rotary evaporator, 20 g of the titanium-silicon composite oxide was added too, and rotated and impregnated for 3 h at 60° C. to perform an ion exchange reaction by alkali metal treatment; when the reaction was accomplished, a catalyst was obtained and recorded as DB-3 after drying for 5 h at 100° C. in air atmosphere and calcinating for 3 h at 500° C. in air, the specific surface area thereof determined by BET was 407 m²/g and the average pore size thereof was 2.6 nm.

COMPARATIVE EXAMPLE 4

100 g of TS-1 molecular sieve (Changling Catalyst Plant of SINOPEC) with a Ti/Si ratio of 1:60 (molar ratio) from which the template agent had been removed was taken, followed by subjecting to the alcohol solution of organic alkali metal salt treatment and the gas-phase silanization treatment according to the same methods as step (3) and step (4) of Example 1 respectively, a catalyst was obtained and recorded as DB-4.

COMPARATIVE EXAMPLE 5

100 g of Ti-MCM-41 molecular sieve (Nankai University Catalyst Plant) with a Ti/Si ratio of 1:50 (molar ratio) from which the template agent had been removed was taken, followed by subjecting to the alcohol solution of organic alkali metal salt treatment and the gas-phase silanization treatment according to the same methods as step (3) and step (4) of Example 1 respectively, a catalyst was obtained and recorded as DB-5.

The catalysts of Examples 1~8 and Comparative Examples 1~5 were characterized by BET, XRF and TGA, the test results of pore size, specific surface area, K element content and silane group content of the catalysts are shown in Table 2. It can be seen that the pore sizes of the catalysts according to the present invention are adjustable and larger than those of the Ti—Si microporous and mesoporous molecular sieve catalysts reported in existing literatures and patents; in addition, both alkali metal modification and silanization modification have been achieved for the catalysts after alkali metal salt solution treatment and gas-phase silanization treatment.

TABLE 2

Characterization results of the catalysts by BET, XRF and TGA

| Catalyst code | Specific surface area m²/g | Average pore size nm | K content wt % | Silane group content wt % |
|---|---|---|---|---|
| A | 422 | 6.5 | 4.6 | 1.8 |
| B | 368 | 10.7 | 4.5 | 1.7 |
| C | 322 | 18.3 | 4.6 | 1.8 |
| D | 406 | 6.2 | 4.6 | 1.9 |
| E | 305 | 18.5 | 8.7 | 1.7 |
| F | 407 | 6.7 | 4.6 | — |
| G | 411 | 6.6 | — | 1.7 |
| H | 387 | 6.7 | 4.6 | 1.9 |
| DB-1 | 413 | 2.7 | — | 1.8 |
| DB-2 | 405 | 2.6 | 4.6 | 1.8 |
| DB-3 | 407 | 2.6 | 4.6 | — |
| DB-4 | 542 | 0.6 | 4.5 | 1.7 |
| DB-5 | 489 | 2.3 | 4.6 | 1.6 |

Figure 1:
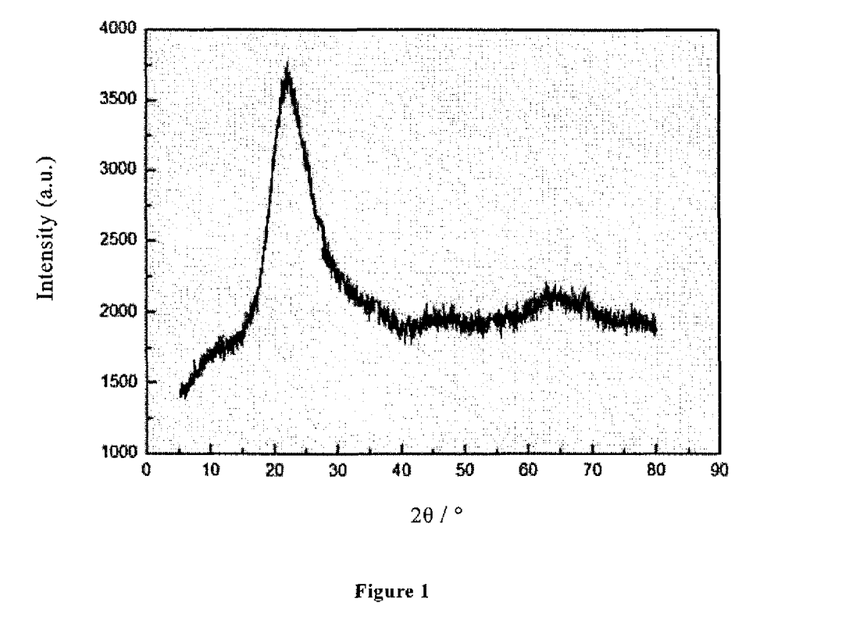
FIG. 1 shows an XRD spectrum of the catalyst prepared in Example 1.

An XRD spectrum of Catalyst A prepared in Example 1 was determined, the result is shown in FIG. 1. It can be seen there is a big peak packet only around 2θ=25° for the obtained Catalyst A, while no other obvious diffraction peaks appear, it is indicated that Catalyst A has an amorphous structure.

Figure 2:
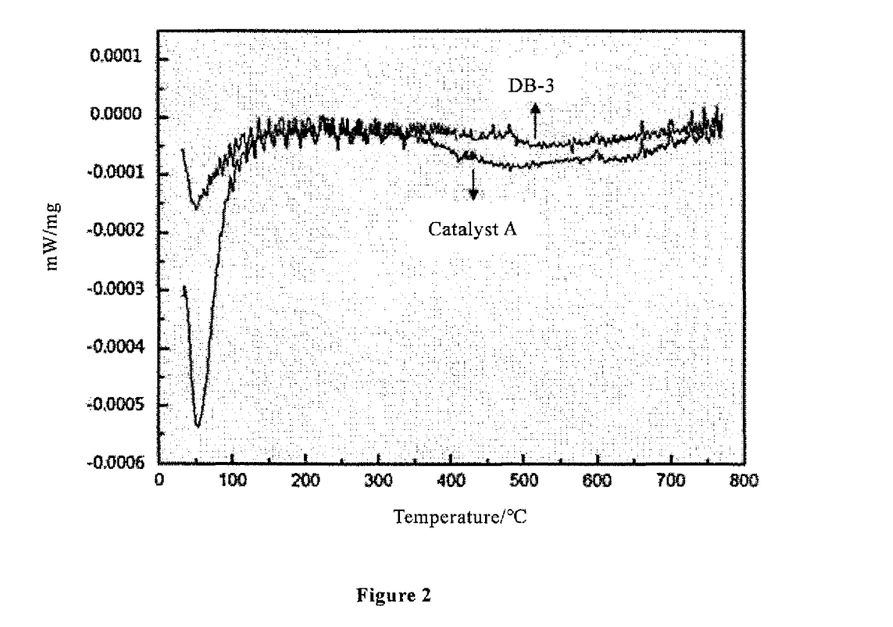
FIG. 2 shows thermogravimetric DSC (scanning calorimetry analysis) curves of the catalyst prepared in Example 1 which was subjected to a silanization treatment and the catalyst prepared in Comparative Example 3 which was not subjected to a silanization treatment respectively.

The thermogravimetric DSC curves of Catalyst A prepared in Example 1 and Catalyst DB-3 prepared in Comparative Example 3 were determined, which are shown in FIG. 2. It can be seen that compared with Catalyst DB-3 which was not subjected to silanization treatment, for Catalyst A which was subjected to silanization treatment, there is an obvious endothermic valley around 400~700° C. which is caused by silane group removal, and it is proved that the silanization modification to the catalyst was achieved in step (4) of Example 1.

EXAMPLE 9

A fixed-bed reactor with an inner diameter of 30 mm was used to fill with each catalyst of Examples 1~8 and Comparative Examples 1~5 respectively with a filling amount of 20 g; epoxidation reaction was conducted by using propylene as raw material, the feed rate of propylene ($C_3H_6$) was 80 g/hr, the concentration of CHP (cumyl hydroperoxide) solution was 35%, the feed quantity of CHP solution was 103.5 g/hr, the molar ratio of $C_3H_6$/CHP was 8:1, the reaction pressure was 4.0 MPa, and the reaction temperature was 60° C. The reaction results are shown in Table 3.

As shown in Table 3, among the catalysts prepared in Examples and Comparative Examples, Catalyst A and Catalyst D with small pore sizes prepared by the method of the present invention have higher selectivity for epoxypropane. In terms of the conversion rates of CHP, the catalysts obtained from Examples of the present invention are obviously higher than those obtained from Comparative Examples; each Example is basically equivalent except Example 8.

Particularly, compared with Catalyst A prepared in Example 1, Catalyst DB-2 prepared in Comparative Example 2 was just not subjected to pore-enlarging treatment; in Comparative Examples 1 and 3, only one modification method was performed except that pore-enlarging treatment was not conducted; in Comparative Examples 4 and 5, both alkali metal modification and silanization modification were conducted to the existing titanium silicalite microporous and mesoporous molecular sieves. According to Table 3, the conversion rates of CHP and the selectivity for epoxypropane of all above five Comparative Examples are significantly lower than those of Catalyst A. It can be seen that the catalysts of the present invention can be used for catalyzing the epoxidation reaction of propylene to produce better effects after pore-enlarging treatment and two modifications according to the present invention.

In addition, compared with Catalyst A prepared in Example 1, Catalyst F prepared in Example 6 only was not processed with alcohol solution of organic alkali metal salt; Catalyst G prepared in Example 7 only was not subjected to silanization treatment. According to Table 3, the above two Examples can achieve similar high conversion rates of CHP as Catalyst A, but the selectivity for epoxypropane are significantly lower than that of Catalyst A. It can be seen that in this reaction, pore-enlarging treatment is conducive to improving the conversion rate of CHP, while the obtained catalyst which was processed by alcohol solution of organic alkali metal salt and gas-phase silanization simultaneously is more conducive to improving the selectivity for epoxypropane product.

Furthermore, the difference between Catalyst A prepared in Example 1 and Catalyst H prepared in Example 8 lies in that in the alkali metal modification step, the alcohol solution of organic alkali metal salt was used in Example 1, while the aqueous solution of inorganic alkali metal salt was used in Example 8. As can be seen from the reaction results in Table 3, the use of water as solvent in the alkali metal modification process can lead to the decline of the selectivity for epoxypropane of the catalyst and the conversion rate of CHP.

TABLE 3

Reaction results of Example 9

| Catalyst code | Average pore size nm | Conversion rate of CHP % | Selectivity for epoxy-propane % |
|---|---|---|---|
| A | 6.5 | 99.2 | 95.5 |
| B | 10.7 | 99.3 | 93.8 |
| C | 18.3 | 99.1 | 91.7 |
| D | 6.2 | 99.4 | 95.3 |
| E | 18.5 | 99.3 | 90.9 |
| F | 6.7 | 99.1 | 90.3 |
| G | 6.6 | 99.2 | 91.7 |
| H | 6.7 | 96.7 | 92.4 |
| DB-1 | 2.7 | 97.2 | 90.6 |
| DB-2 | 2.6 | 96.6 | 93.2 |
| DB-3 | 2.6 | 97.0 | 92.7 |
| DB-4 | 0.6 | 52.1 | 85.3 |
| DB-5 | 2.3 | 95.2 | 91.8 |

EXAMPLE 10

A fixed-bed reactor with an inner diameter of 30 mm was used to fill with each catalyst of Examples 1~8 and Comparative Examples 1~5 respectively with a filling amount of 20 g; the feed rate of 1-decene ($C_{10}H_{20}$) was 80 g/hr, the concentration of CHP solution was 35%, the feed quantity of CHP solution was 41.34 g/hr, the molar ratio of $C_{10}H_{20}$/CHP was 6:1, the reaction pressure was normal pressure, and the reaction temperature was 80° C. The reaction results are shown in Table 4.

It can be seen from Table 4: among the catalysts prepared in Examples and Comparative Examples, Catalyst B with medium pore size prepared by the method of the present invention has higher conversion rate of CHP and selectivity for 1,2-epoxydecane. However, in each Comparative Example, the conversion rate of CHP shows a sharp decline compared with the result of Example 9. It can be seen that the pore size of Catalyst B after pore-enlarging treatment is advantageous for the reaction for preparing 1,2-epoxydecane.

TABLE 4

Reaction results of Example 10

| Catalyst code | Average pore size nm | Conversion rate of CHP % | Selectivity for 1,2-epoxy-decane % |
|---|---|---|---|
| A | 6.5 | 92.8 | 93.5 |
| B | 10.7 | 99.3 | 94.8 |
| C | 18.3 | 99.1 | 92.7 |
| D | 6.2 | 93.4 | 94.3 |
| E | 18.5 | 99.3 | 91.8 |
| F | 6.7 | 92.5 | 90.1 |
| G | 6.6 | 91.9 | 89.6 |
| H | 6.7 | 92.5 | 90.3 |
| DB-1 | 2.7 | 63.8 | 88.6 |
| DB-2 | 2.6 | 63.6 | 88.5 |
| DB-3 | 2.6 | 63.1 | 88.2 |
| DB-4 | 0.6 | 20.3 | 90.5 |
| DB-5 | 2.3 | 61.7 | 90.2 |

EXAMPLE 11

A fixed-bed reactor with an inner diameter of 30 mm was used to fill with each catalyst of Examples 1~8 and Comparative Examples 1~5 respectively with a filling amount of 20 g; the feed rate of cyclododecatriene was 80 g/hr, the concentration of CHP solution was 35%, the feed quantity of CHP solution was 41.34 g/hr, the molar ratio of $C_{10}H_{20}$/CHP was 6:1, the reaction pressure was normal pressure, and the reaction temperature was 80° C. The reaction results are shown in Table 5.

It can be seen from Table 5: among the catalysts prepared in Examples and Comparative Examples, Catalyst C and Catalyst E with large pore sizes prepared by the method of the present invention have higher conversion rates of CHP and selectivity for CDDO (cyclododecatriene oxide). However, in each Comparative Example, the conversion rate of CHP shows a decline compared with the result of Example 10. It can be seen that the pore sizes of Catalyst C and Catalyst E after pore-enlarging treatment are advantageous for the reaction for preparing CDDO.

TABLE 5

Reaction results of Example 11

| Catalyst code | Average pore size nm | Conversion rate of CHP % | Selectivity for CDDO % |
|---|---|---|---|
| A | 6.5 | 89.2 | 92.5 |
| B | 10.7 | 94.2 | 93.7 |
| C | 18.3 | 99.2 | 94.5 |
| D | 6.2 | 88.4 | 91.3 |
| E | 18.5 | 99.5 | 93.9 |
| F | 6.7 | 88.9 | 88.5 |
| G | 6.6 | 90.0 | 86.6 |
| H | 6.7 | 82.4 | 87.9 |
| DB-1 | 2.7 | 36.5 | 85.6 |
| DB-2 | 2.6 | 36.5 | 85.3 |
| DB-3 | 2.6 | 35.9 | 84.0 |
| DB-4 | 0.6 | 16.3 | 88.2 |
| DB-5 | 2.3 | 30.6 | 90.3 |

According to the above-mentioned Examples, the pore sizes of the obtained catalysts can be controlled by adjusting the treatment temperature and time in the pore-enlarging treatment step, so that they can adapt to epoxidation reactions of the olefin reactants with different molecular sizes. Compared with the catalysts whose pore sizes are incompatible with the molecule sizes of the reactants, the titanium-silicon composite oxide of the present invention which is subjected to pore-enlarging treatment can improve the conversion rates of the reactants and the selectivity for epoxidation product when used as a catalyst. In addition, by using alcohol solution of organic alkali metal salt and silane to modify the titanium-silicon composite oxide after pore-enlarging treatment, the selectivity for epoxidation product of the catalyst can be further improved.

The invention claimed is:

1. A preparation method for an olefin epoxidation catalyst, comprising the following steps:
   (1) mixing a silicon ester solution, a titanium ester solution and a surfactant, adjusting pH to 6~7 by using diluted acid in order to achieve a complete hydrolysis of the silicon ester, and aging to obtain a titanium-silicon composite gel;
   (2) adding organic amine or liquid ammonia to the gel, performing pore-enlarging treatment under constant temperature condition with a treatment temperature of 60~150° C., and drying, calcinating in air atmosphere to obtain an amorphous titanium-silicon composite oxide;
   (3) subjecting the titanium-silicon composite oxide to impregnation by using an alcohol solution of organic alkali metal salt, and drying, calcinating in air atmosphere to obtain a titanium-silicon composite oxide modified by alkali metal; and (4) subjecting the titanium-silicon composite oxide modified by alkali metal obtained in step (3) to a gas-phase silanization treatment by using an organic silanization reagent with $N_2$ as carrier gas;

to give the olefin epoxidation catalyst.

2. The preparation method for an olefin epoxidation catalyst according to claim 1, wherein,
   in step (1), the molar ratio of the silicon ester to the titanium ester is 10~60:1, and the addition amount of the surfactant is 0.5~5.0 wt % based on the total weight of the silicon ester and the titanium ester;
   in step (2), the mass ratio of the organic amine or liquid ammonia to the gel is 1:5~1:10, and the treatment time of the pore-enlarging treatment is 3~12 h, the amorphous titanium-silicon composite oxide with an average pore size of 5~20 nm is obtained accordingly.

3. The preparation method for an olefin epoxidation catalyst according to claim 2, wherein,
   in step (3), the concentration of the alcohol solution of organic alkali metal salt is 2~5 wt %; the mass ratio of the alcohol solution of organic alkali metal salt to the titanium-silicon composite oxide is 5:1~10:1; the impregnation temperature is 40~80° C., and the impregnation time is 1~5 h;
   in step (4), the weight ratio of the organic silanization reagent to the titanium-silicon composite oxide modified by alkali metal is 0.01~0.2; the temperature of the gas-phase silanization treatment is 200~400° C. and the processing time is 2~6 h.

4. The preparation method for an olefin epoxidation catalyst according to claim 1, wherein, in step (1),
   i) the silicon ester is one or more selected from the group consisting of tetraethyl silicate, ethyl orthosilicate and butyl silicate; the mass concentration of the silicon ester solution is 30~60 wt % wherein the solvent is ethanol or isopropanol;
   ii) the titanium ester is one or more selected from the group consisting of tetraethyl titanate, tetrapropyl titanate, tetrabutyl titanate, and tetraisopropyl titanate; the concentration of the titanium ester solution is 10~30 wt % wherein the solvent is n-butanol or isopropanol;
   iii) the surfactant is one or more selected from the group consisting of hexadecyl trimethyl ammonium bromide, P-123 triblock copolymer, sodium dodecyl sulfonate, polyacrylamide, polyethylene glycol and polypropylene glycol;
   iv) the diluted acid is one selected from the group consisting of nitric acid, hydrochloric acid and acetic acid.

5. The preparation method for an olefin epoxidation catalyst according to claim 1, wherein, in step (1), the surfactant is firstly added to the silicon ester solution and mixed evenly, then the titanium ester solution is slowly added to the silicon ester solution under the condition that the stirring speed of a stirring reactor is 3000~5000 r/min.

6. The preparation method for an olefin epoxidation catalyst according to claim 1, wherein, in step (1), the aging temperature is 40~120° C. and the aging time is 2~8 h.

7. The preparation method for an olefin epoxidation catalyst according to claim 1, wherein, in step (2), the organic amine is one or more selected from the group consisting of ethylamine, ethylenediamine, propylamine, and n-butylamine.

8. The preparation method for an olefin epoxidation catalyst according to claim 1, wherein, in step (2), the drying temperature is 80~160° C. and the drying time is 3~6 h; the calcinating temperature is 400~600° C., and the calcinating time is 3~6 h.

9. The preparation method for an olefin epoxidation catalyst according to claim 1, wherein, in step (3), the organic alkali metal salt is one or more selected from the group consisting of sodium methoxide, sodium ethoxide, potassium ethoxide, sodium tert-butoxide and potassium tert-butoxide; the alcohol used as solvent in the alcohol solution of the organic alkali metal salt is one or more selected from the group consisting of methanol, ethanol and tert-butanol.

10. The preparation method for an olefin epoxidation catalyst according to claim 1, wherein, in step (3), the drying temperature is 80~160° C. and the drying time is 3~6 h; the calcinating temperature is 300~500° C. and the calcinating time is 3~6 h.

11. The preparation method for an olefin epoxidation catalyst according to claim 1, wherein, in step (4), the organic silanization reagent is one or more selected from the group consisting of hexamethyldisilazane, hexamethylchlorosilazane, heptamethylchlorosilazane, trimethylchlorosilane, dimethylchlorosilane, tetramethyldisilazane, dimethyldiethoxysilane, trimethylmethoxysilane, dimethyldimethoxysilane and trimethylethoxysilane.

12. An olefin epoxidation catalyst, which is an amorphous titanium-silicon composite oxide, wherein, the molar ratio of $SiO_2$ to $TiO_2$ contained is 10~60:1 by stoichiometry; alkali metal element and/or silane group are also comprised in the catalyst with a mass percentage of 1~10% respectively; the titanium-silicon composite oxide has an average pore size of 5~20 nm, and a specific surface area of 200~600 m$^2$/g.

13. A method for olefin epoxidation reaction, wherein the catalyst prepared by the preparation method for an olefin epoxidation catalysts according to claim 1 is used in the epoxidation reaction.

14. The preparation method for an olefin epoxidation catalyst according to claim 3, wherein,
   in step (3), the impregnation temperature is 50~70° C., and the impregnation time is 2~4 h.

15. The preparation method for an olefin epoxidation catalyst according to claim 1, wherein,
   in step (2), the calcinating temperature is 450~550° C.;
   in step (4), the organic silanization reagent is hexamethyldisilazane.

16. An olefin epoxidation catalyst according to claim 12, wherein alkali metal element and/or silane group are also comprised in the catalyst with a mass percentage of 1~10% respectively;
   the titanium-silicon composite oxide has a specific surface area of 300~450 m$^2$/g.

17. The method for olefin epoxidation reaction according to claim 13, wherein the olefin is C3~C16 linear or isomerized olefin, or C6~C16 cycloolefin or aromatic olefin; the oxidant used in the epoxidation reaction is an organic peroxide; and the epoxidation reaction is a liquid-phase epoxidation reaction of the olefin and the organic peroxide.

18. The method for olefin epoxidation reaction according to claim 17, wherein the oxidant used in the epoxidation reaction is tert-butyl hydrogen peroxide, ethylbenzene hydrogen peroxide or cumyl hydroperoxide.

\* \* \* \* \*